United States Patent
Yuan et al.

(10) Patent No.: US 11,763,500 B2
(45) Date of Patent: Sep. 19, 2023

(54) PHOTOACOUSTIC IMAGE RECONSTRUCTION METHOD FOR SUPPRESSING ARTIFACTS

(71) Applicant: NANJING UNIVERSITY, Nanjing (CN)

(72) Inventors: Jie Yuan, Nanjing (CN); Xiang Ma, Nanjing (CN); Yunhao Zhu, Nanjing (CN); Chengwen Guo, Nanjing (CN)

(73) Assignee: Nanjing University, Nanjing (CN)

( * ) Notice: Subject to any disclaimer, the term of this patent is extended or adjusted under 35 U.S.C. 154(b) by 404 days.

(21) Appl. No.: 17/277,355

(22) PCT Filed: Sep. 17, 2019

(86) PCT No.: PCT/CN2019/106051
§ 371 (c)(1),
(2) Date: Mar. 18, 2021

(87) PCT Pub. No.: WO2020/082934
PCT Pub. Date: Apr. 30, 2020

(65) Prior Publication Data
US 2022/0028128 A1 Jan. 27, 2022

(30) Foreign Application Priority Data
Oct. 25, 2018 (CN) .......................... 201811298045.6

(51) Int. Cl.
*G06T 11/00* (2006.01)
*A61B 5/00* (2006.01)

(52) U.S. Cl.
CPC .......... *G06T 11/005* (2013.01); *A61B 5/0095* (2013.01); *G06T 11/006* (2013.01)

(58) Field of Classification Search
CPC ....... G06T 11/005; G06T 11/006; G06T 5/00; G06T 15/00; G06T 11/00; G06T 15/005; A61B 5/0095; A61B 2576/00
See application file for complete search history.

(56) References Cited

U.S. PATENT DOCUMENTS

| 2013/0331680 A1 | 12/2013 | Furukawa |
| 2018/0177461 A1* | 6/2018 | Bell ..................... A61B 5/7267 |
| 2022/0028128 A1* | 1/2022 | Yuan ..................... G06T 11/006 |

FOREIGN PATENT DOCUMENTS

| CN | 107180442 A | 9/2017 |
| CN | 108573474 A | 9/2018 |

(Continued)

OTHER PUBLICATIONS

Y. Zhang, Z. Tang, Y. Wu and F. D. J. Zhang, "Axial Signal Analysis and Image Reconstruction in Acoustic Lens Photoacoustic Imaging System," in IEEE Access, vol. 5, pp. 918-923, 2017, doi: 10.1109/ACCESS.2016.2619359.

*Primary Examiner* — Daniel Pihulic
(74) *Attorney, Agent, or Firm* — Hsuanyeh Law Group P.C.

(57) ABSTRACT

The present disclosure provides a photoacoustic image reconstruction method for suppressing artifacts, including: acquiring relevant parameters of the system; selecting a suitable pixel size and dividing the imaging area into multiple pixels; traversing each pixel, calculating multiple delay and summations according to the time sequence, and restoring the signal waveform; calculating the signal envelope of the signal recovered from each pixel, performing signal suppression, suppressing artifacts in the signal, and retaining real signal; the real signal value in the suppressed signal is taken as the gray value of the pixel in the image, and is saved in the picture to complete the reconstruction of the image.

9 Claims, 2 Drawing Sheets

(56) References Cited

FOREIGN PATENT DOCUMENTS

| | | | | |
|---|---|---|---|---|
| CN | 111192335 A * | 5/2020 | ........... | A61B 5/0095 |
| JP | 2018143764 A | 9/2018 | | |
| WO | 2018056187 A1 | 6/2019 | | |
| WO | WO-2020082934 A1 * | 4/2020 | ........... | A61B 5/0095 |

* cited by examiner

PHOTOACOUSTIC IMAGE RECONSTRUCTION METHOD FOR SUPPRESSING ARTIFACTS

RELATED APPLICATIONS

This is a U.S. national phase of International Application No. PCT/CN2019/106051, filed on Sep. 19, 2019, which claims priority to Chinese Patent Application No. 20181298045.6, filed on Oct. 25, 2018, the entire contents of both of which are incorporated herein by reference for all purposes.

TECHNICAL FIELD

The invention relates to the fields of optics, acoustics, biomedicine, signal processing and image processing, and particularly relates to a photoacoustic image reconstruction method for suppressing artifacts.

BACKGROUND TECHNIQUE

Non-destructive image reconstruction methods are needed in various fields, such as medicine, military, and material monitoring. Among them, photoacoustic imaging, as a new imaging method, reflects the light absorption distribution of substances in the imaging area. The current popular real-time photoacoustic imaging method is a basic delay and summation method, which is simple and fast. However, the delay and summation (DAS) method will bring obvious artifacts in the picture and affect the quality of the picture. Therefore, it is very important to reduce the artifacts in the reconstruction method while maintaining the real-time imaging of the method.

SUMMARY OF THE INVENTION

Purpose of the invention: The technical problem to be solved by the present invention is to remove the artifacts in the photoacoustic image through the method of multiple delay and summation based on time sequence.

In order to solve the above technical problem, the present invention discloses a photoacoustic image reconstruction method for suppressing artifacts, which includes the following steps:

Step 1: Acquire relevant parameters of the system and collect photoacoustic signals from the imaging area.

Step 2: Select an appropriate pixel size and divide the imaging area into multiple pixels.

Step 3: Calculate multiple delay and summations for each pixel according to the sequence of time, restore the waveform of the pixel signal, and calculate the signal envelope.

Step 4: Perform signal suppression on the signal envelope recovered from each pixel to suppress artifact signals and retain the real signal.

Step 5: Use the real signal value as the gray value of the pixel in the image, save it in the picture, and finally complete the image reconstruction.

In the present invention, in step 1, the relevant parameters of the acquisition system include the sampling frequency of the sensor $f_s$, the number of sensor units N, and the actual physical location of each sensor, $r_n^{tr}$, n=1, 2, 3, . . . , N. After obtaining the sensor parameters, guide the laser to irradiate the imaging (target) area, and use the sensor to collect the signal of each sensor $s_n^{tr}(t)$, n=1, 2, 3, . . . , N.

In the present invention, in step 2, the selected pixel size is $\Delta r$. The imaging area is divided into M pixel blocks according to the selected pixel size, and the actual physical location of each pixel is $r_m^p$, m=1, 2, 3, . . . , M.

In the present invention, in step 3, for each pixel, the beam signal of the pixel is restored: for the number m pixel, first calculate the distance between the pixel and each sensor, which is defined as $d(m,n)=|r_m^p - r_n^{tr}|$, n=1, 2, 3, . . . , N, then calculate the delay of sound from the position of the pixel to each sensor based on the distance $$\tau(m, n) = \frac{|r_m^p - r_n^{tr}|}{c_0},$$

n=1, 2, 3, . . . , N, where $c_0$ is the speed of sound; use the calculated delay to find the corresponding signal in the sensor, and restore the beamforming signal of the pixel $$s_m^p(t) = \sum_{n=1}^{N} s_n^{tr}(t + \tau(m, n));$$

after the signal is recovered, the Hilbert transform is used to extract the signal envelope $Env_m(t)=H[s_m^p(t)]|$.

In the present invention, in step 4, suppressing the artifact components in the signal: first locate the maximum value in the corresponding pixel envelope signal $Env_m^{max}=\max(Env_m(t))$, select the appropriate suppression coefficient k, the suppression coefficient k is used to control the intensity of signal suppression, and calculate the suppressed signal $$Env_m^{sup}(t) = Env_m(t) \cdot \left(\frac{Env_m(t)}{Env_m^{max}}\right)^k.$$

In the present invention, in step 5, the real signal value of the suppressed signal at time zero $Env_m^{sup}(0)$ is selected as the grayscale value of the pixel in the image, and is saved in the image; calculate the suppressed signal for each pixel $Env_m^{sup}(0)$, m=1, 2, 3, . . . , M, and finally complete the image reconstruction.

In the present invention, there is no need for redundant signal acquisition, only the laser is required to irradiate the imaging (target) area, and the photoacoustic signal generated is collected by the sensor at the same time, and the image can be reconstructed.

In the present invention, the calculation of the time delay only needs the positions of the sensors, and there is no special requirement on the shape of the sensors and the distribution of the sensors.

In the present invention, it is necessary to select an appropriate suppression coefficient k to suppress noise and artifact signals, and the suppression coefficient k is used to control the degree of suppression. The larger the value, the stronger the suppression effect on noise and artifacts.

In the present invention, calculations only involve basic calculations and fast Fourier transforms, and at the same time, the calculation of each pixel is independent of each other, has extremely high parallelizability, and is suitable for real-time imaging.

In the present invention, the reconstruction method is suitable for both two-dimensional and three-dimensional reconstruction.

DESCRIPTION OF THE DRAWINGS

The present invention will be further described below in conjunction with the drawings and specific example, and the advantages of the above and/or other aspects will become clearer.

DETAILED EXAMPLE DESCRIPTION

Figure 1:
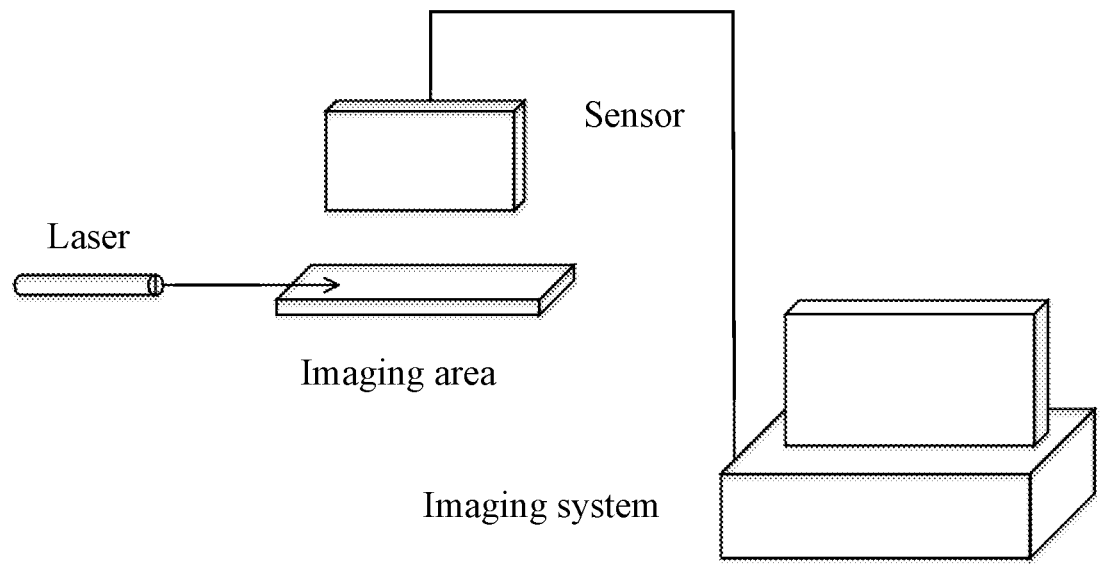
FIG. 1 is a schematic diagram of signal acquisition in accordance with an embodiment.
Figure 2:
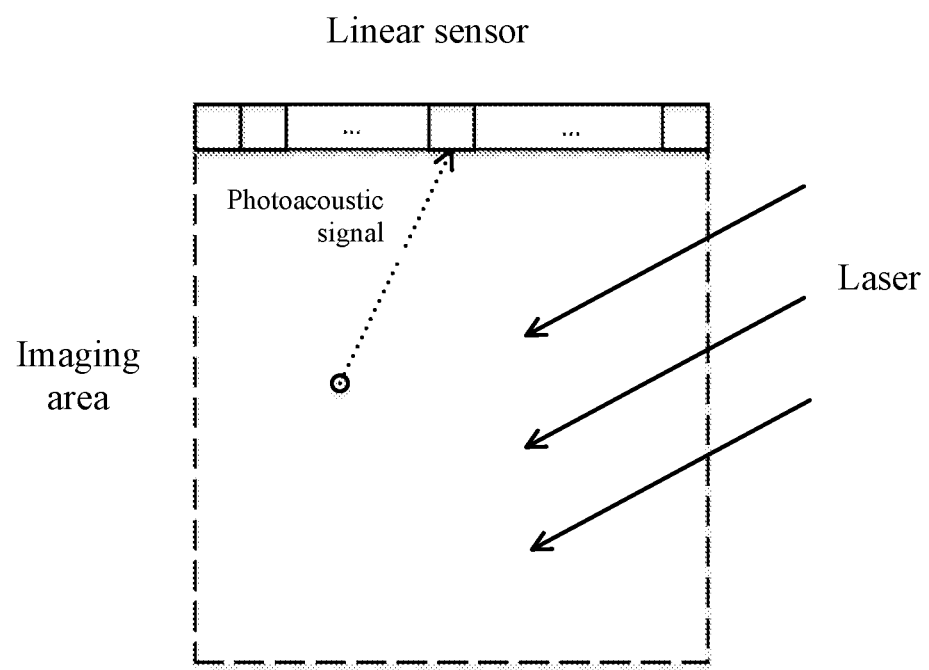
FIG. 2 is a schematic diagram of a linear sensor in accordance with an embodiment.
Figure 3:
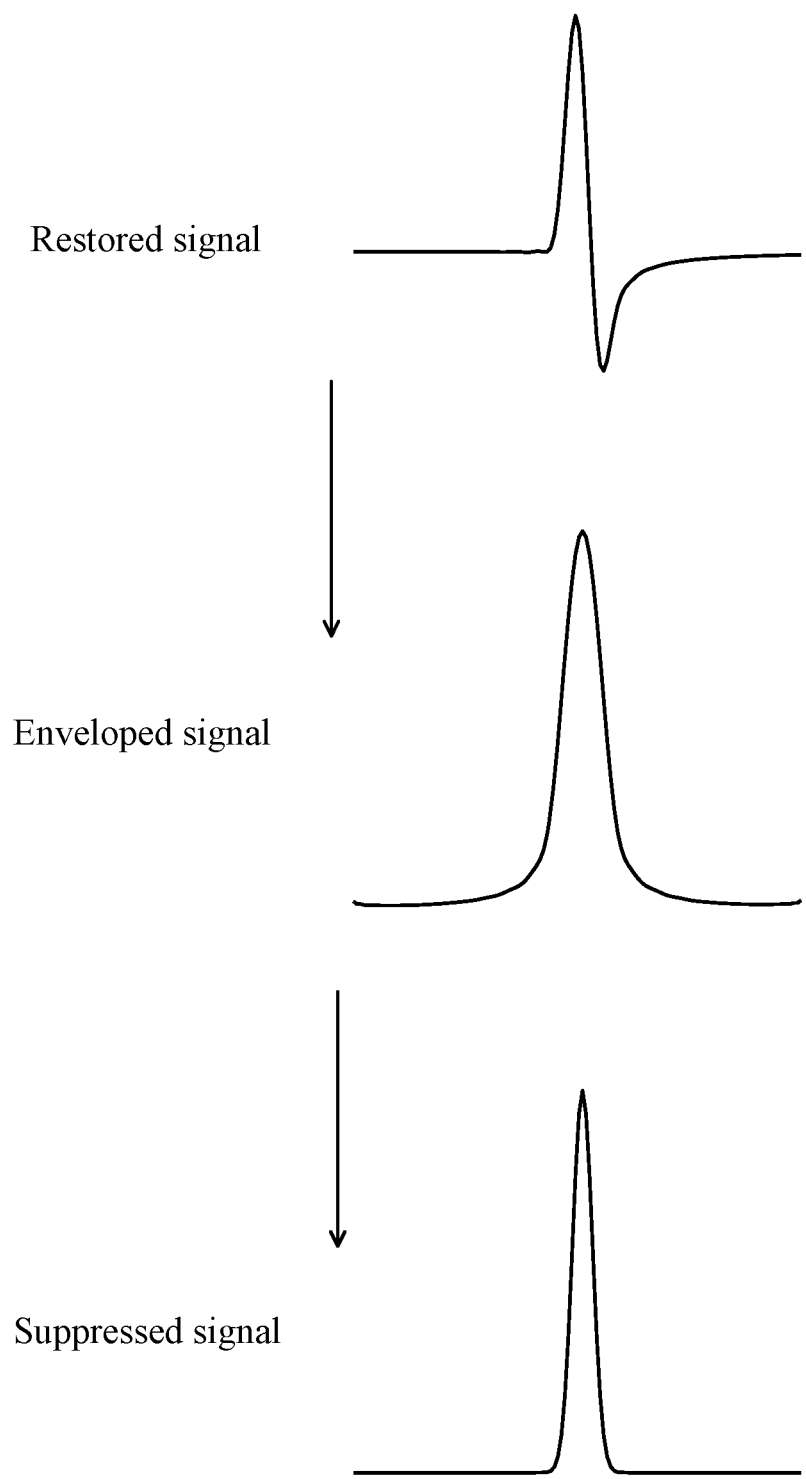
FIG. 3 is a schematic diagram of signal extraction envelope and suppression in accordance with an embodiment.

Purpose of the invention: The technical problem to be solved by the present invention is to remove the artifacts in the photoacoustic image through the method of multiple delay and summation based on time sequence.

In order to solve the above technical problem, the present invention discloses a photoacoustic image reconstruction method for suppressing artifacts, which includes the following steps:

Step 1: Acquire relevant parameters of the system and collect photoacoustic signals from the imaging area.

Step 2: Select an appropriate pixel size and divide the imaging area into multiple pixels.

Step 3: Calculate multiple delay and summations for each pixel according to the sequence of time, restore the waveform of the pixel signal, and calculate the signal envelope.

Step 4: Perform signal suppression on the signal envelope recovered from each pixel to suppress artifact signals and retain the real signal.

Step 5: Use the real signal value as the gray value of the pixel in the image, save it in the picture, and finally complete the image reconstruction.

In this example, in step 1, the relevant parameters of the acquisition system include the sampling frequency of the sensor $f_s$, the number of sensor units N, and the actual physical location of each sensor is $r_n^{tr}$, n=1, 2, 3, . . . , N. In this example, a linear sensor probe with 128 channels (sensors) is selected, the interval between adjacent sensor units is 0.298 mm, and the sampling frequency is 28.98 MHz, then the actual physical location of the sensor unit is $r_n^{tr}$=(0.298× (n−0.5) mm, 0 mm), n=1, 2, 3, . . . , N. After obtaining the sensor and system parameters, these parameters are stored in static space as invariants. The imaging area is a 25 mm×25 mm square two-dimensional area under the linear sensor, and the sensor is used to control the laser to irradiate the middle part of the imaging area, and the signal of each sensor $s_n^{tr}(t)$, n=1, 2, 3, . . . , 128 is collected.

In this example, in step 2, the selected pixel size is Δr=(0.1 mm, 0.1 mm). That is, the physical size corresponding to each pixel is 0.1 mm×0.1 mm, and the imaging area is divided into 250×250 pixel blocks according to the selected pixel size, which gives rise to 62,500 total pixels. The pixel coordinate of the m-th pixel is ($\lfloor$m/250$\rfloor$+1, m mod 250), m=1, 2, 3, . . . , M, then the actual physical location of each pixel is $r_m^p$=(0.1×($\lfloor$m/250$\rfloor$+0.5) mm, 0.1×((m mod 250)−0.5) mm), m=1, 2, 3, . . . , M.

In this example, in step 3, for each pixel, the beam signal of the pixel is restored: for the number m, m=1, 2, 3, . . . , 62500 pixel, first calculate the distance between the pixel and each sensor, which is d(m,n)=|$r_m^p$−$r_n^{tr}$|, n=1, 2, 3, . . . , N, where we have the value of $r_n^{tr}$=(0.298×(n−0.5) mm, 0 mm), $r_m^p$=(0.1×($\lfloor$m/250$\rfloor$+0.5) mm, 0.1×((m mod 250)−0.5) mm), then calculate the delay of sound from the position of the pixel to each sensor based on the distance $$\tau(m, n) = \frac{|r_m^p - r_n^{tr}|}{c_0},$$

n=1, 2, 3, . . . , N, where $c_0$ is the speed of sound. $c_0$ is related to the current medium and temperature, in this example, the imaging area is located in water, the temperature is 20° C., and the sound velocity at this time is 1.482 mm/us; use the calculated delay to find the corresponding signal in the sensor, and restore the beamforming signal of the pixel $$s_m^p(t) = \sum_{n=1}^{N} s_n^{tr}(t + \tau(m, n));$$

after the signal is recovered, the Hilbert transform is used to extract the signal envelope $Env_m(t)$=|H[$s_m^p(t)$]|. Hilbert transform can be realized by Fourier transform. Here, because the signal is a discrete sampling point, it can be realized by fast Fourier transform, and the processing time can fully meet the real-time imaging; in order to reduce the calculation time, when recovering the signal $$s_m^p(t) = \sum_{n=1}^{N} s_n^{tr}(t + \tau(m, n)),$$

only the signal from the τ(m,n) to the front and the back 128 points is intercepted, and the envelope is calculated for the signal of these 256 points.

In this example, in step 4, suppressing the artifact components in the signal: first locate the maximum value in the corresponding pixel envelope signal $Env_m^{max}$=max($Env_m$(t)), In this example, the default maximum value appears near time 0, that is, in the center of the 256 signal points. Therefore, the maximum value is searched from 128 points to both sides. When the first peak occurs, the peak value is considered to be the maximum value. Select the appropriate suppression coefficient k, the suppression coefficient k is used to control the intensity of signal suppression, defining k as an integer value can reduce the computational complexity. In this example select k=3, and calculate the suppressed signal $$Env_m^{sup}(t) = Env_m(t) \cdot \left(\frac{Env_m(t)}{Env_m^{max}}\right)^3.$$

In this example, in step 5, the real signal value of the suppressed signal at time zero $Env_m^{sup}(0)$ is selected as the grayscale value of the pixel in the image and is saved in the image; calculate the suppressed signal $Env_m^{sup}(0)$, m=1, 2, 3, . . . , M for each pixel in a total of 62,500 pixels. For the pixels where the artifacts and noises are located, the maximum signal value deviates from the zero time, so the suppressed signal will be suppressed at the zero time, while the signal of the non-artifact and noise pixels will not be suppressed at the zero time, so as to finally complete the reconstruction of the image, as well as the suppression of noise and artifacts.

In this example, there is no need for redundant signal collection, only the laser is required to irradiate the imaging area, and the photoacoustic signal generated is collected by the sensor at the same time to reconstruct the image.

In the present invention, the delay calculation only needs the positions of the sensors, and there is no special requirement on the shape of the sensors and the distribution of the sensors. Therefore, in addition to the linear sensor in this example, other sensors such as ring sensors and three-dimensional sensors are also applicable.

In the present invention, it is necessary to select an appropriate suppression coefficient to suppress noise and artifact signals, and the suppression coefficient is used to control the degree of suppression. The larger the value, the stronger the suppression effect on noise and artifacts.

The above-mentioned multiple delay and summation methods can add the sensor directivity coefficient and distance coefficient for accurate calculation. At the same time, the calculation of each pixel in this method does not depend on each other, so that a high degree of parallelization can be achieved, and the time to reconstruct the picture can be greatly reduced. The theoretical minimum calculation time does not depend on the number of pixels since each pixel is parallelized. So it can be carried out real-time and fast imaging. In this method, the calculation only involves basic operations and fast Fourier transform, and the calculation of each pixel is independent of each other, which is extremely parallelizable, and is suitable for real-time imaging.

The present invention proposes a photoacoustic image reconstruction method that suppresses artifacts. The form of the required laser and ultrasonic device are not limited in this patent; the number of ultrasonic sensors used, and the location of each sensor are not limited in this patent; the relative positions of the sensors, laser and imaging area are not limited in this patent; the software and hardware implementation of the method are not limited in this patent. For those of ordinary skill in the field, several improvements and modifications can be made without departing from the principle of the invention, and these should also be regarded as the protection scope of the present invention. In addition, all the components that are not clear in this example can be implemented using existing technology.

What is claimed is:

1. A method for suppressing artifacts in a photoacoustic image, comprising:
   providing physical properties of a photoacoustic sensor and collecting photoacoustic signals $s_n^{tr}(t)$, n=1, 2, 3, . . . , N from an imaging target area using the photoacoustic sensor;
   selecting a pixel size for the imaging target area and dividing the imaging target area into multiple pixels;
   calculating multiple delays and summations for each of said multiple pixels according to a time sequence, restoring a waveform of the multiple pixels, and calculating a signal envelope of the multiple pixels;
   performing signal suppression on the signal envelope recovered from each of said multiple pixels to suppress artifact signals, thereby recovering a real signal value for each of said multiple pixels; and
   using the real signal value as a grayscale value for each of the multiple pixels in the photoacoustic image, thereby reconstructing the photoacoustic image.

2. The method according to claim 1, wherein physical properties of the photoacoustic sensor include a sampling frequency ($f_s$) of the photoacoustic sensor, a quantity (N) of sensor units of the photoacoustic sensor, and physical locations of the sensor units ($r_n^{tr}$, n=1, 2, 3, . . . , N).

3. The method according to claim 1, wherein the selected pixel size is $\Delta r$, the imaging target area is divided into M pixel blocks according to the selected pixel size, and physical locations of the multiple pixels are defined as $r_m^p$, m=1, 2, 3, . . . , M.

4. The method according to claim 1, wherein restoring the waveform of the multiple pixels comprises, for the m-th pixel, first calculating a distance between the m-th pixel and each of the sensor units, the distance being defined as $d(m,n)=|r_m^p-r_n^{tr}|$, n=1, 2, 3, . . . , N, then calculating a time delay of sound from the m-th pixel to each of the sensor units, the time delay being defined as $$\tau(m, n) = \frac{|r_m^p - r_n^{tr}|}{c_0},$$

n=1, 2, 3, . . . , N, where $c_0$ is the speed of sound, thereafter using the calculated time delay to find a corresponding signal in the sensor, and restoring a beamforming signal of the m-th pixel using $$s_m^p(t) = \sum_{n=1}^{N} s_n^{tr}(t + \tau(m, n)).$$

5. The method according to claim 1, wherein performing the signal suppression comprises locating a maximum value in the signal envelope $Env_m^{max}=\max(Env_m(t))$, selecting a suppression coefficient k to control signal suppression intensity, and calculating a suppressed signal using $$Env_m^{sup}(t) = Env_m(t) \cdot \left(\frac{Env_m(t)}{Env_m^{max}}\right)^k.$$

6. The method according to claim 5, wherein the real signal value is the suppressed signal at time zero $Env_m^{sup}(0)$.

7. The method according to claim 1, further comprising, before collecting the photoacoustic signals, irradiating a laser light onto the imaging target area.

8. The method according to claim 4, wherein calculating the signal envelope of the multiple pixels comprises, after the beamforming signal is stored, extracting the signal envelope from the beamforming signal using a Hilbert transform $Env_m(t)=|H[s_m^p(t)]|$.

9. The method of claim 5, wherein calculating the suppressed signal comprises calculating the suppressed signal for each of the multiple pixels at time zero, $Env_m^{sup}(0)$, m=1, 2, 3, . . . , M, thereby completing image reconstruction.

* * * * *